United States Patent
Kastner

(10) Patent No.: US 8,283,635 B2
(45) Date of Patent: Oct. 9, 2012

(54) METHOD FOR DETERMINING THE GAS QUALITY OF A SAMPLE GAS MIXED AT LEAST IN PART WITH BIOGAS OR PROCESSED BIOGAS

(75) Inventor: Joachim Kastner, Dortmund (DE)

(73) Assignee: Elster GmbH, Dortmund (DE)

( * ) Notice: Subject to any disclaimer, the term of this patent is extended or adjusted under 35 U.S.C. 154(b) by 0 days.

(21) Appl. No.: 12/737,223

(22) PCT Filed: Jun. 18, 2009

(86) PCT No.: PCT/DE2009/000855
§ 371 (c)(1),
(2), (4) Date: Dec. 20, 2010

(87) PCT Pub. No.: WO2009/152819
PCT Pub. Date: Dec. 23, 2009

(65) Prior Publication Data
US 2011/0215247 A1      Sep. 8, 2011

(30) Foreign Application Priority Data
Jun. 21, 2008  (DE) .......................... 10 2008 029 553

(51) Int. Cl.
*G01J 5/02*   (2006.01)
(52) U.S. Cl. ................................. 250/339.07
(58) Field of Classification Search .............. 250/338.1, 250/339.06, 339.07, 339.08
See application file for complete search history.

(56) References Cited

U.S. PATENT DOCUMENTS

| | | | |
|---|---|---|---|
| 6,490,908 B2 | 12/2002 | Schley | |
| 6,552,793 B1 | 4/2003 | Kastner | |
| 6,941,230 B1 | 9/2005 | Stirnberg et al. | |
| 7,216,486 B2 | 5/2007 | Doebbeling et al. | |
| 2004/0195531 A1 | 10/2004 | Rahmouni et al. | |

FOREIGN PATENT DOCUMENTS

| | | |
|---|---|---|
| DE | 101 21 641 | 4/2002 |
| EP | 1 141 677 | 10/2001 |
| EP | 1 147 396 | 10/2001 |

(Continued)

OTHER PUBLICATIONS

International Search Report, mailed Dec. 11, 2009.

(Continued)

*Primary Examiner* — Mark R Gaworecki
(74) *Attorney, Agent, or Firm* — Collard & Roe, P.C.

(57) ABSTRACT

The invention relates to a method for determining the gas quality of a sample gas mixed at least in part with biogas, having the main components $CH_4$, $CO_2$, $N_2$, $O_2$, $H_2$, proceeding from a spectrum of the sample gas determined by means of infrared-spectroscopy measurement methods, under operating conditions, from which the mole ratios of the sample gas are determined by means of correlative methods, and converted to characteristic variables of the gas quality. In this connection, the optical absorption of methane $CH_4$ and carbon dioxide $CO_2$ and the heat conductivity $\lambda$ of the sample gas are measured, the mole ratio $xCH_4$ is determined from the absorption of the $CH_4$, the mole ratio $xCO_2$ is determined from the absorption of the $CO_2$, the mole ratios of nitrogen $xN_2$, of oxygen $xO_2$ and of hydrogen $xH_2$ that are not detected optically are determined from the mole ratios $xCH_4$, $xCO_2$ and the heat conductivity $\lambda$, by means of a correlation calculation $\lambda = F(xCH_4, xCO_2, xN_2, xO_2, xH_2)$, whereupon characteristic parameters of the sample gas are calculated from the mole ratios obtained in this way.

17 Claims, 2 Drawing Sheets

FOREIGN PATENT DOCUMENTS

WO    WO 03/062618    7/2003

OTHER PUBLICATIONS

Figure 1:
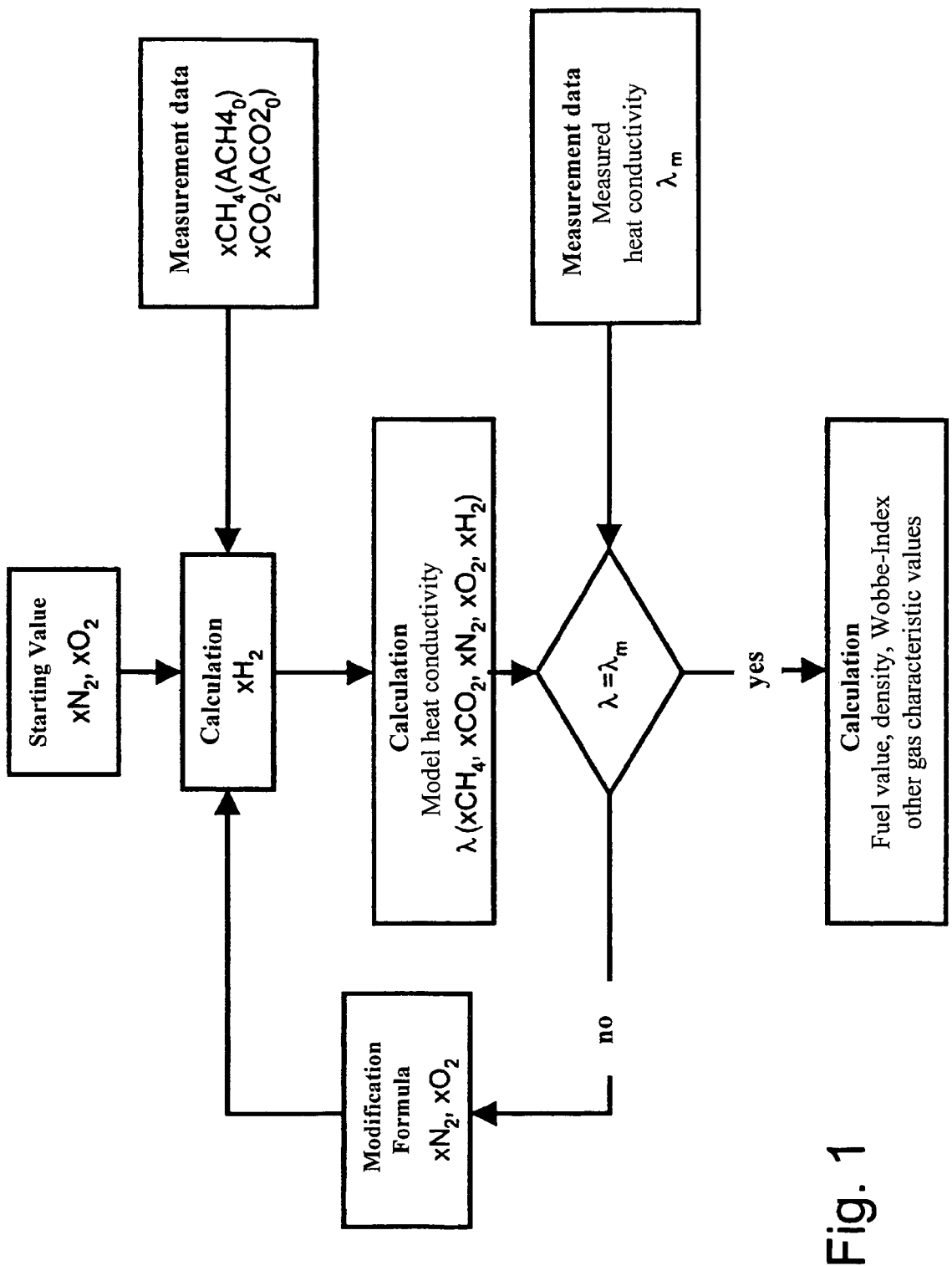

Analyse und Bewertung der Nutzungsmöglichkeiten von Biomasse {Analysis and evaluation of the utilization possibilities of biomass}, Wuppertal Institut für Klima Umwelt Energie: {Wuppertal Institute for Climate, Environment, Energy}, 2005. (Spec, pgs. 3 and 23).

DVGW Arbeitsblatt G 262 {DVWG Work Paper G 262}: Nutzung von Gasen aus regenerativen Quellen in der öffentlichen Gasversorgung {Utilization of gases from regenerative sources in the public gas supply}, Nov. 2004. Spec, pgs. 1, 2, 4, 5 and 23).

METHOD FOR DETERMINING THE GAS QUALITY OF A SAMPLE GAS MIXED AT LEAST IN PART WITH BIOGAS OR PROCESSED BIOGAS

CROSS REFERENCE TO RELATED APPLICATIONS

This application is the National Stage of PCT/DE2009/000855 filed on Jun, 18, 2009, which claims priority under 35 U.S.C. §119 of German Application No. 10 2008 029 553.1 filed on Jun. 21, 2008, the disclosure of which is incorporated by reference. The international application under PCT article 21(2) was not published in English.

The invention relates to a method for determining the gas quality of a sample gas mixed at least in part with biogas or processed biogas, in accordance with the preamble of claim 1.

Biogas from biomass represents a regenerative, $CO_2$-neutral energy medium. The biogas economy is therefore being publicly subsidized in Germany and in the EU.

A widespread and very efficient use of biogas is combustion in combined heat and power plants. By means of the coupling of power and heat, a high overall degree of effectiveness is achieved, to the extent that there is a practical use for the heat emitted. If the heat is not used at the location of the biogas production, it is more efficient, in terms of the overall degree of effectiveness, to transport the biogas to the location where the heat is used and to combust it there. The transport can take place by means of feed into the natural gas network. The conditions for gas quality and the billing measurements were regulated in G262 [2], in cooperation between the natural gas and biogas economy.

Biogas is produced by means of fermentative or thermal processes. In the case of fermentative production, organic material (garbage, liquid manure, energy plants (NaWaRo=RRM renewable raw materials), sewage treatment sludge, animal material) is decomposed by means of bacteria, to produce gas. The gases that form contain $CH_4$ and $CO_2$ as the lead materials (see Table 1):

TABLE 1

Composition of the gases from biogas, sewage treatment gas, and dump gas systems (reference values)

| Origin | Main components | | | Gas accompanying substances** | | | $H_2O$ | Operating data of the system | |
|---|---|---|---|---|---|---|---|---|---|
| | $CH_4$ Vol-% | $CO_2$ Vol-% | $O_2/N_2$ Vol-% | KW*) mg/m³ | $H_2S$ mg/m³ | FCKW*) mg/m³ | dewpoint °C. | $P_n$ mbar | t °C. |
| Biogas systems | 50-85 | 50-15 | remainder | — | to ca. 10 000 | — | ca. 35 | to ca. 50 | ca. 35 |
| Sewage treatment gas systems | 65-70 | 35-20 | remainder | to ca. 10 | to ca. 10 000 | — | ca. 35 | to ca. 50 | ca. 35 |
| Garbage dump | 40-60 | 40-20 | remainder | to ca. 300 | to ca. 900 | 20 to ca. 1000 | ca. 25 | 0 to 3 | ca. 25 |

*)KW = hydrocarbons (C number >2); FCKW = fluorochlorohydrocarbons
**In addition, other gas accompanying substances can occur, depending on possible co-fermentation In thermal production, the biomaterial is gasified by means of being heated with air as the gasification medium or under air exclusion (pyrolysis). The lead components of these synthesis gases are $H_2$, CO, $CO_2$, $N_2$ (see Table 2, G262 [2]).

TABLE 2

Composition (main components) of gases from thermal gas production methods
(reference values, revised extract from [Lit. 10]}

| Gasification method and gasification medium | Fuel value MJ/m³ | Composition | | | | | | |
|---|---|---|---|---|---|---|---|---|
| | | $H_2$ Vol-% | CO Vol-% | $CH_4$ Vol-% | $CO_2$ Vol-% | $N_2$ Vol-% | $H_2O$ Vol-% | KW Vol-% |
| Packed bed: oxygen (FbS) | 9.3-9.7 | 35-43 | 13-34 | 0-12 | 19-35 | 0-2 | to 3 | 0-3 |
| Fluidized bed: air (WbL) | 5-7 | 4-20 | 9-22 | 1-7 | 14-16 | to 56 | 0-3 | 0-2 |
| Fluidized bed: oxygen (WbS) | 9-12 | 40-45 | 29-34 | to 3 | 19-22 | 0-2 | to 3 | to 2 |
| Entrained bed method: oxygen (FeS) | 10-12 | 30-35 | 50-70 | to 1 | 2-15 | 0-2 | to 3 | to 1 |
| Pyrolysis (Pyr) | 7-15 | 4-46 | 18-40 | to 15 | 15-20 | 0 | <1 | to 4 |

Thermal production has found only limited use until now. In a current study [1], however, thermo-chemical production of biogas is mentioned as a new option, in order to significantly increase the biogas potential by means of better availability of wood as a raw material. The resulting synthesis gas is supposed to be brought to feed-in quality in a subsequent catalytic methanation process. No information is given in the study with regard to the gas composition, particularly with regard to the $H_2$ concentration.

Processing and analysis of the raw synthesis gases is more complex, due to the numerous lead components, than in the case of fermentative gases. The raw biogas must be processed further both for use on location and for feed into gas transport networks, so that no disruption or damage of the systems being used occurs, and so that no products harmful to health or the environment are formed during combustion. The requirements concerning gas quality for feed into the network have been regulated in G262 [2]. Accordingly, biogas is allowed to be fed into the public gas supply if it has been processed correctly, as an additional or replacement gas.

In the case of feed into H-gas networks (other than Russian gas), the processed biogas (H<11.064 kWh/m$^3$) must be conditioned by means of mixing in liquid gas (LPG=Liquid Petroleum Gas, propane/butane). In this case, the calibratable measurement takes place after the liquid gas is mixed in. In this connection, the measurement serves primarily for guaranteeing the gas composition, in each instance, in the gas network, which can change as the result of mixing in the biogas, and for accounting of the gas amounts fed in, with regard to the amounts of heat that can be produced with it.

The design approvals for commercially available gas composition measurement devices up to now do not automatically cover the measurement of biogas. Above all, the effect of hydrogen $H_2$, which cannot be entirely excluded, is problematic in this connection (typically 125 . . . 250 ppm, much 500 . . . 700 ppm, peak 2000 ppm).

According to G262 [2], the biogas must be measured according to calibration law so that it can be introduced into public gas transport networks. This relates not only to the volume measurement but also to measurement of the gas composition.

First, a distinction is made between the measurement technology for the energy measurement according to calibration law and for monitoring of parameters of product quality ($xO_2$, $xH_2S$). In an ideal case, the two measurement tasks are integrated into one device.

To measure the gas composition, many devices and measurement methods have been developed over the course of time, whereby increasingly, devices and methods are used in which the absorption of the gas with reference to infrared radiation is utilized. Such devices and methods are known, for example, from EP 1 141 677 B1 and 1 147 396 B1. In this connection, correlative methods are used, by means of which the measured absorption of the infrared radiation is converted to the variables of the gas, in each instance, and thus operation-specific variables of the gas can be determined. With regard to the details of such methods, explicit reference is made to EP 1 141 677 B1 and 1 147 396 B1, and these are also made an object of this application.

It is problematic with regard to the use of such devices and methods for measuring the gas composition of biogas that the biogas can contain small amounts of $H_2$. While it is true that fermenter gases should be free of $H_2$ (see Table 1, G262 [2]), it is known from practice, however, that processed biogases can contain 150 . . . 500 ppm, in peaks 2000 ppm $H_2$. Accordingly, the Physikalisch-Technische Bundesanstalt (PTB) {German Federal Institute for Physical Technology} requires a study with corresponding $H_2$ admixture for the approval of biogas for feed into gas networks.

The correlative methods used until now are based on a heat conductivity measurement that reacts sensitively to the high heat conductivity of $H_2$.

It is therefore the task of the present invention to further develop the methods for measurement of the gas composition, of the type stated, in such a manner that they are also suitable for measuring biogas or processed biogas, without hydrogen $H_2$ or other admixtures present in biogas or added to biogas, such as oxygen $O_2$ or liquid gas LPG leading to impermissible changes in the measurement values.

The solution of the task according to the invention is evident from the characterizing features of claim 1 in interaction with the characteristics of the preamble. Further advantageous embodiments of the invention are evident from the dependent claims.

The invention proceeds from a method for determining the gas quality of a sample gas mixed at least in part with biogas or processed biogas, having the main components $CH_4$, $CO_2$, $N_2$, $O_2$, $H_2$, proceeding from a spectrum of the sample gas determined under operating conditions, by means of infrared-spectroscopy measurement methods, from which the mole ratios of the sample gas are determined by means of correlative methods, and converted to characteristic values of the gas quality. Such a method, of the type stated, is further developed in that the optical absorption of methane $CH_4$ and of carbon dioxide $CO_2$ and the heat conductivity $\lambda$ of the sample gas, and, if liquid gas LPG is mixed in, the optical absorption of the LPG are measured, the mole ratio $xCH_4$ is determined from the absorption of the $CH_4$, and the mole ratio $xCO_2$ is determined from the absorption of the $CO_2$, the mole ratios of nitrogen $xN_2$, of oxygen $xO_2$ and of hydrogen $xH_2$ that are not detected optically are determined from the mole ratios $xCH_4$, $xCO_2$ and the heat conductivity $\lambda$, and, if liquid gas LPG is mixed in, from the mole ratio xLPG, by means of a correlation calculation $\lambda=F(xCH_4,xCO_2,xN_2,xO_2,xH_2)$ or $\lambda=F(xCH_4, xCO_2, xN_2, xO_2, xH_2,xLPG)$, whereupon characteristic parameters of the sample gas are calculated from the mole ratios obtained in this way. It is particularly advantageous in this method of procedure that the mole ratios of nitrogen $N_2$, oxygen $O_2$ and hydrogen $H_2$ can be determined, on the basis of the measurable values for the components methane $CH_4$ and of carbon dioxide $CO_2$ of the sample gas and the measurement of its heat conductivity $\lambda$ and, if liquid gas LPG is mixed in, of the optical absorption of the LPG, using the correlation calculation, by means of a simple linear formula, in that in the case of a linear formula, the proportion of the hydrogen $H_2$ can be calculated directly, analytically (or also in the case of a non-linear formula, the correlation calculation is carried out until the value for the heat conductivity $\lambda$ that proceeds from the correlation calculation corresponds to the measured value). Using the linear formula, it is therefore possible to analytically determine the mole ratios that were unknown until then, of nitrogen $N_2$, oxygen $O_2$ and hydrogen $H_2$ in the sample gas, and from that, characteristic variables of the sample gas such as gross calorific value, net calorific value, density, Wobbe index, methane number, or the like. In this connection, the linear formula for the correlation of the gas components can be carried out in simple and therefore fast manner, and requires only manageable computer power. Only the values for the absorption of methane $CH_4$ and of carbon dioxide $CO_2$ and the heat conductivity $\lambda$ of the sample gas, and, if liquid gas LPG is mixed in, also the optical absorption of the LPG are required as measurement values. In the case of alternative use of a non-linear formula and the numerical solution that becomes necessary with this, starting values for the mole ratios of nitrogen $xN_2$ and oxygen $xO_2$ are required, on the basis of which a starting value for the mole ratio of the hydrogen $H_2$ can be calculated. Using these starting values and the measured values, the correlation calculation can be carried out iteratively, by means of adapting the values for mole ratios of nitrogen $xN_2$ and oxygen $xO_2$, and can be adapted, in each instance, by means of a comparison of the calculated heat conductivity $\lambda$ and the measured heat conductivity $\lambda_m$. If the values for calculated heat conductivity $\lambda$ and measured heat conductivity $\lambda_m$ agree, the actual mole ratios of nitrogen $N_2$, oxygen $O_2$ and hydrogen $H_2$ are present, and the other characteristic variables of the sample gas can be calculated from them, using physical laws.

It is advantageous for implementation of the method if a linear formula is selected from the mole ratios for the correlation $\lambda = F(xCH_4, xCO_2, xN_2, xO_2, xH_2)$:

$$\lambda = \lambda_0 + xCH_4 \cdot \lambda CH_4 + xCO_2 \cdot \lambda CO_2 + xN_2 \cdot \lambda N_2 + xO_2 \cdot \lambda O_2 + xH_2 \cdot \lambda H_2$$

Such a formula is simple in terms of computation technology, can be carried out analytically, and requires relatively little computer power. As a result, this formula can be carried out quickly during operation, and the results of the correlation and thus the characteristic variables to be determined are quickly available.

In this connection, the parameters $\lambda_0$, $\lambda CH_4$, $\lambda CO_2$, $\lambda(N_2, O_2)$, $\lambda H_2$ are the generally formulated fit parameters of linear modeling, and can be determined as follows: For a number of gases having a known composition and known reference heat conductivity, the model heat conductivity is calculated according to the linear formula. In this connection, it is advantageous if the fit parameters are optimized in a manner known to every person skilled in the art, in such a way that a minimal deviation between the model heat conductivity and the reference heat conductivity is obtained for all gases. The parameters $\lambda CH_4$, $\lambda CO_2$, $\lambda(N_2,O_2)$, $\lambda H_2$ can be interpreted as heat conductivities of the pure substances or substance group, in each instance. In this connection, the parameter $\lambda_0$ is an origin heat conductivity of the linear model and permits that the model function does not have to pass through the coordinate origin (axis section).

Alternatively, if LPG is added to the sample gas, a linear formula can be selected from the mole ratios also for the correlation $\lambda = F(xCH_4, xCO_2, xN_2, xO_2, xH_2, xLPG)$:

$$\lambda = xCH_4 \cdot \lambda CH_4 + xCO_2 \cdot \lambda CO_2 + xN_2 \cdot \lambda N_2 + xO_2 \cdot \lambda O_2 + xH_2 \cdot \lambda H_2 + xLPG \cdot \lambda LPG$$

Such a formula can also be calculated analytically, and therefore quickly and easily yields results for the required variables of the sample gas.

It can be advantageous for implementation of the method if a polynomial formula with terms of a higher order and mixed terms is selected from the mole ratios for the correlation $\lambda = F(xCH_4, xCO_2, xN_2, xO_2, xH_2)$ or $\lambda = F(xCH_4, xCO_2, xN_2, xO_2, xH_2, xLPG)$. While it is true that such a polynomial formula is more complicated to calculate as compared with the above formula, it possibly yields greater accuracy of the results. Here, the solution to the formula of the correlation can take place by way of a polynomial formula, by means of numerical iteration.

For both formulas of the correlation calculation, it is advantageous if the measured heat conductivity $\lambda_m$ and the calculated heat conductivity $\lambda$ are compared with one another by means of iterative variation and calculation of the unknown mole ratios $xN_2$, $xO_2$, $xH_2$. In this connection, the essentially matching agreement of the measured heat conductivity $\lambda_m$ and the calculated heat conductivity $\lambda$ is the criterion on the basis of which the correlation calculation can be terminated. If agreement exists between the measured heat conductivity $\lambda_m$ and the calculated heat conductivity $\lambda$, the precise substance amount distribution of the components of the sample gas not detected by means of measurement technology can be calculated by means of back-calculation, using the formula of the correlation calculation, and the characteristic variables can then be determined from that.

It is furthermore advantageous in carrying out the correlation calculation if the mole ratios $xN_2$ of $N_2$ and $xO_2$ of $O_2$ are determined as the sum $x(N_2,O_2):=xN_2+xO_2$ from the correlation, since the components oxygen and nitrogen are difficult to detect separately from one another, in any case.

The method can also be developed further in that the heat conductivity of the sample gas is measured at two temperatures ($\lambda 1, \lambda 2$), the heat capacity of the sample gas is measured at two temperatures ($C1, C2$), and the mole ratios $xCH_4$, $xCO_2$, $xN_2+xO_2$, $xH_2$ are determined by means of solving a system of correlation equations $$\lambda 1 (xCH_4, xCO_2, xN_2+xO_2, xH_2)$$

$$\lambda 2 = F2(xCH_4, xCO_2, xN_2+xO_2, xH_2)$$

$$C1 = F3(xCH_4, xCO_2, xN_2+xO_2, xH_2)$$

$$C2 = F4(xCH_4, xCO_2, xN_2+xO_2, xH_2)$$

By means of the use of additional measurement variables as well as of a non-linear formula for the correlation, if applicable, other influence variables for the correlation can also be included, which utilize the temperature dependence of the heat capacity and the heat conductivity of the sample gas, and thus allow a separate determination of the mole ratios of nitrogen $xN_2$ and oxygen $xO_2$, if applicable. It is true that this formula is more complicated for the correlation in terms of measurement technology and computer technology, but at the same time, the number of iteration steps in the correlation can be reduced, because of the larger amount of information of the measured values. In this connection, as well, after agreement of the calculated heat conductivity $\lambda$ and the measured heat conductivity $\lambda_m$ has been determined, the characteristic variables of the sample gas that have already been described above can be calculated.

In this connection, it is possible that the heat conductivity $\lambda$ is measured at multiple temperatures of the sample gas, in order to individually determine the mole ratios of $xN_2$, $xO_2$ and $xH_2$. By means of measuring the heat conductivity $\lambda$ at multiple temperatures, advantage can be taken of the fact that due to the temperature dependence of the heat conductivity $\lambda$, measurement technology values can be obtained that can make an improvement in the correlation or even a direct determination of the mole ratios of $xN_2$ and $xO_2$ possible.

The same holds true analogously if the heat capacity is measured, in addition, in order to individually determine the mole ratios of $xN_2$ and $xO_2$. In this connection, as well, the heat capacity can be measured at multiple temperatures of the sample gas, for the reasons already mentioned.

It is furthermore advantageous if the spectral filter for determining the proportions of the hydrocarbons works in the range of essentially 3.33 μm, and does not work in that of 3.46 μm that is otherwise usual for sample gases composed of pure hydrocarbons, since then, the absorption of the infrared radiation in the biogas is particularly advantageous.

Furthermore, it is advantageous for operational safety if the gas quality is monitored with regard to the concentration of oxygen $O_2$ and hydrogen sulfide $H_2S$. In gas line systems, the values for these contaminants of the gas are not allowed to exceed specific values, for example in order not to have a negative influence on the operational safety of the gas transport or the useful lifetime of the gas line system. For this reason, these values can be monitored by means of chemical sensors, for example, particularly by means of electrochemical cells, to determine if specific limit values are exceeded. Likewise, it is possible that monitoring of the sample gas for the concentration of oxygen $O_2$ is carried out by means of laser diodes.

A particularly preferred embodiment of the method according to the invention, for the solution by means of numerical iteration when using a non-linear formula, is shown in the drawing.

Figure 2:
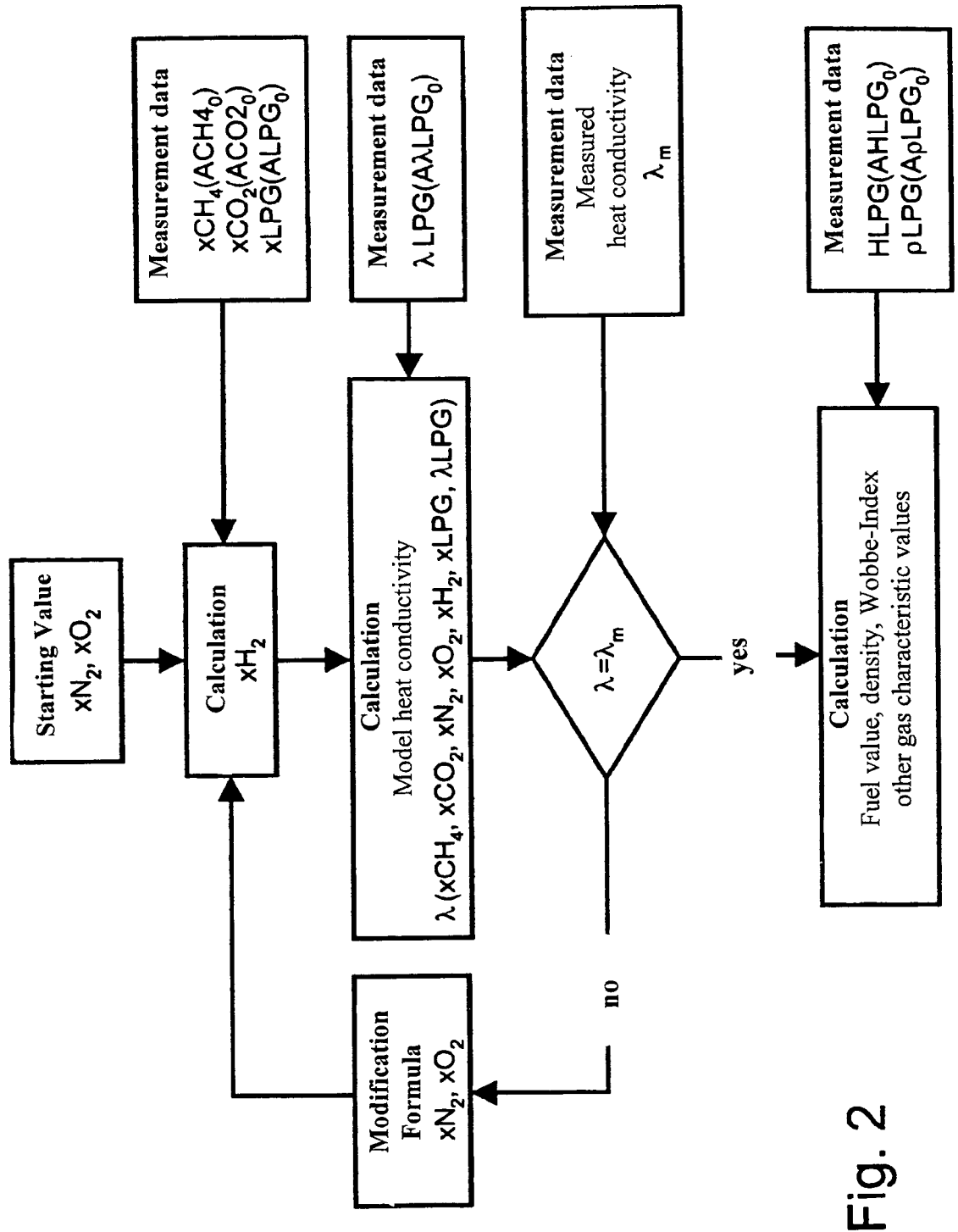

The drawing shows:

FIG. 1—Flow chart of the method for the solution by means of numerical iteration when using a non-linear formula, FIG. 2—Flow chart of the method for the solution by means of numerical iteration when using a non-linear formula, when liquid gas is added to the sample gas.

FIG. 1 describes the fundamental structure of the method with a hydrocarbon component (only $CH_4$) according to claim 1 for the solution by means of numerical iteration when using a non-linear formula.

For this purpose, for the correlation calculation as such, the following physical basics should be formulated in advance:

For the measurement of biogas in feed-in quality according to DVGW-G260, -G262 without LPG admixture, the following formula can be used. The standardization $$xCH_4 xCO_2 xN_2 + xO_2 + xH_2 = 1 \quad \text{Equ. 1}$$

applies.

Gross calorific value and density are calculated as follows:

$$H = xCH_4 \cdot HCH_4 + xH_2 \cdot HH_2 \quad \text{Equ. 1}$$

$$\rho = xCH_4 \cdot \rho CH_4 + xCO_2 \cdot \rho CO_2 + xN_2 \cdot \rho N_2 + xO_2 \cdot \rho O_2 + xH_2 \cdot \rho H_2 \quad \text{Equ. 2}$$

The mole fractions $xCH_4$ and $xCO_2$ are determined directly from optical absorption measurements, according to the Beer-Lambert law. In this connection, if necessary, special characteristic lines that deviate from the pure Beer-Lambert law must be taken into consideration (F1, F2 are empirical calibration functions):

$$xCH_4 = F1(ACH4_0) \quad \text{Equ. 4}$$

$$xCO_2 = F2(ACO2_0) \quad \text{Equ. 5}$$

$ACH4_0$ and $ACO2_0$ are the optical absorptions with reference to a reference state $(p_0, T_0)$. Suitable absorption bands lie in the infrared spectral range; typical ranges are: hydrocarbons 3.1-3.6 μm, $CO_2$ 4.2-4.4 μm.

The concentrations of $H_2$, $N_2$ and $O_2$ can be determined from the measurement of the heat conductivity $\lambda$, the standardization condition Equ. 1, and the following model calculation. For the heat conductivity of the gas, a linear mixture formula is made:

$$\lambda = xCH_4 \cdot \lambda CH_4 + xCO_2 \cdot \lambda CO_2 + xN_2 \cdot \lambda N_2 + xO_2 \cdot \lambda O_2 + xH_2 \cdot \lambda H_2 \quad \text{Equ. 6}$$

The concentrations $xN_2$ and $xO_2$ can only be determined as a sum, the terms are therefore combined to $x(N_2,O_2) := x(N_2) + x(O_2)$.

The heat conductivity of the partial mixture $(N_2, O_2)$ is designated as $\lambda(N_2, O_2)$.

Equation 6 therefore reads:

$$\lambda = xCH_4 \cdot \lambda CH_4 + xCO_2 \cdot \lambda CO_2 + x(N_2,O_2) \cdot \lambda(N_2,O_2) + xH_2 \cdot \lambda H_2 \quad \text{Equ. 7}$$

The heat conductivities of $N_2$ and $O_2$ are very similar, so that the heat conductivity of $N_2$ is used as an approximation for the partial mixture $(N_2, O_2)$:

$$\lambda = xCH_4 \cdot \lambda CH_4 + xCO_2 \cdot \lambda CO_2 + x(N_2,O_2) \cdot \lambda N_2 xH_2 \cdot \lambda H_2 \quad \text{Equ. 8}$$

The standardization condition can be transposed as follows:

$$x(N_2,O_2) = 1 - xCH_4 - xCO_2 - xH_2 \quad \text{Equ. 9}$$

Insertion of Equ. 9 into Equ. 8 and solving yields the mole fraction $xH_2$ $$xH_2 = \frac{\lambda - xCH_4 \cdot (\lambda CH_4 - \lambda N_2) - xCO_2 \cdot (\lambda CO_2 - \lambda N_2) - \lambda N_2}{\lambda H_2 - \lambda N_2} \quad \text{Equ. 10}$$

The concentration of the hydrogen $xH_2$ can thus be determined from the measurement variables, therefore the concentration $x(N_2, O_2)$ can also be calculated according to Equation 9.

Thus, the mole fractions of all the gas components have been determined, and the target variables H, ρ can be calculated analytically.

In the case of alternative use of a non-linear formula and the numerical solution that becomes necessary in this connection, according to FIG. 1, starting values for the correlation for the mole ratios of nitrogen $xN_2$ and oxygen $xO_2$ are needed, on the basis of which a starting value for the mole ratio of the hydrogen $H_2$ can be calculated. Using these starting values and the measured values, the correlation calculation can then be carried out iteratively, by means of adaptation of the values for mole ratios of nitrogen $xN_2$ and oxygen $xO_2$, and can be adapted, in each instance, by means of a comparison of the calculated heat conductivity $\lambda$ and the measured heat conductivity $\lambda_m$. If the values of calculated heat conductivity $\lambda$ and measured heat conductivity $\lambda_m$ agree, the actual mole ratios of nitrogen $N_2$, oxygen $O_2$ and hydrogen $H_2$ are present, and then the other characteristic variables of the sample gas can be calculated using physical laws.

For adaptation of the gas characteristic values of biogas to the feed-in network, air and liquid gas (LPG=Liquid Petroleum Gas, propane/butane) can be mixed in. If only air is mixed in, the method described above is suitable.

If LPG is mixed in, the linear formula must be modified in that the influence of the liquid gas must also be taken into consideration. The contribution of liquid gas can be determined by means of an additional spectral measurement, in which the wavelength of the infrared filter is coordinated with the absorption bands of the higher hydrocarbons (propane and butane). The formula expands as follows:

$$xCH_4 xCO_2 xN_2 + xO_2 + xH_2 + xLPG = 1 \quad \text{Equ. 11}$$

$$H = xCH_4 \cdot HCH_4 + xH_2 \cdot HH_2 + xLPG \cdot HLPG \quad \text{Equ. 12}$$

$$\rho = xCH_4 \cdot \rho CH_4 + xCO_2 \cdot \rho CO_2 + xN_2 \cdot \rho N_2 + xO_2 \cdot \rho O_2 + xH_2 \cdot \rho H_2 + xLPG \cdot \rho LPG \quad \text{Equ. 13}$$

The mole fractions $xCH_4$, $xCO_2$ and $xLPG$ are calculated directly from optical absorption measurements, using the Beer-Lambert law. In this connection, any special characteristic lines that deviate from the pure Beer-Lambert law must also be taken into consideration (F1, F2, F3 are empirical calibration functions):

$$xCH_4 = F1(ACH_0) \quad \text{Equ. 14}$$

$$xCO_2 = F2(ACO2_0) \quad \text{Equ. 15}$$

$$xLPG = F3(ALPG_0) \quad \text{Equ. 16}$$

$ACH4_0$, $ACO2_0$ and $ALPG_0$ are the optical absorptions with reference to a reference state ($p_0$, $T_0$). Suitable absorption bands lie in the infrared spectral range; typical ranges are: hydrocarbons 3.1-3.6 µm, particularly higher hydrocarbons (such as propane, butane, for example) 3.3-3.5 µm, $CO_2$ 4.2-4.4 µm.

The concentrations of $H_2$, $N_2$ and $O_2$ can be determined from the measurement of the heat conductivity $\lambda$, the standardization condition Equ. 11, and the following model calculation. For the heat conductivity of the gas, a linear mixture formula is made:

$$\lambda = xCH_4 \cdot \lambda CH_4 + xCO_2 \cdot \lambda CO_2 + xN_2 \cdot \lambda N_2 + xO_2 \cdot \lambda O_2 + xH_2 \cdot \lambda H_2 + xLPG \cdot \lambda LPG \quad \text{Equ. 17}$$

LPG is typically a mixture of propane and butane. If the composition of the LPG is unknown, the properties of this mixture, specifically the gross calorific value HLPG, the density ρLPG, and the heat conductivity λLPG are also not known. Therefore the determination from further optical absorption measurements of the hydrocarbons is used. For this purpose, the absorbance is measured in further spectral ranges, if necessary, and further calibration functions F4, F5 and F6 are defined:

$$HLPG = F4(AHLPG_0) \quad \text{Equ. 18}$$

$$\rho LPG = F5(A\rho LPG_0) \quad \text{Equ. 19}$$

$$\lambda LPG = F6(A\lambda LPG_0) \quad \text{Equ. 20}$$

Since LPG essentially consists only of hydrocarbons, the gross calorific value and the density of the mixture are strongly correlated. As an alternative to the measurement according to Equ. 19, the density can be used as a function of the gross calorific value:

$$\rho LPG = F7(HLPG) \quad \text{Equ. 21}$$

The concentrations $xN_2$ and $xO_2$ can only be determined as a sum, the terms are therefore combined to $x(N_2,O_2):=x(N_2)+x(O_2)$.

The heat conductivity of the partial mixture ($N_2$, $O_2$) is indicated with $\lambda(N_2, O_2)$.

Equation 17 therefore reads:

$$\lambda = xCH_4 \cdot \lambda CH_4 + xCO_2 \cdot \lambda CO_2 + x(N_2,O_2) \cdot \lambda(N_2,O_2) + xH_2 \cdot \lambda H_2 + xLPG \cdot \lambda LPG \quad \text{Equ. 22}$$

The heat conductivities of $N_2$ and $O_2$ are very similar, so that the heat conductivity of $N_2$ is used as an approximation for the partial mixture ($N_2$, $O_2$):

$$\lambda = xCH_4 \cdot \lambda CH_4 + xCO_2 \cdot \lambda CO_2 + x(N_2,O_2) \cdot \lambda N_2 + xH_2 \cdot \lambda H_2 + xLPG \cdot \lambda LPG \quad \text{Equ. 23}$$

The standardization condition can be transposed as follows:

$$x(N_2,O_2) = 1 - xCH_4 - xCO_2 - xH_2 - xLPG \quad \text{Equ. 24}$$

Inserting Equ. 24 into Equ. 23 and solving yields the mole fraction $xH_2$ $$xH_2 = \frac{\lambda - xCH_4 \cdot (\lambda CH_4 - \lambda N_2) - xCO_2 \cdot (\lambda CO_2 - \lambda N_2) - xLPG \cdot (\lambda LPG - \lambda N_2) - \lambda N_2}{\lambda H_2 - \lambda N_2} \quad \text{Equ. 25}$$

The concentration of the hydrogen $xH_2$ can thus be determined from the measurement variables, and with this, the concentration $x(N_2, O_2)$ can also be calculated according to Equ. 24.

Thus, the mole fractions of all the gas components have been determined, and the target variables H, p can be calculated.

FIG. 2 describes the fundamental sequence of the method with two hydrocarbon components ($CH_4$+liquid gas (LPG: C3,C4)) for the solution by means of numerical iteration when using a non-linear formula, as it can be present, for example, in the conditioning of biogas by means of feeding in air and LPG.

Formulas for refining and varying the methods described can be implemented as follows, for example:

1. The formulas for heat conductivity Equ. 6, Equ. 17 can be refined with terms of a higher order, and refined with mixed terms. An analytical solution might then no longer be possible. The unknowns $xH_2$ and $x(N_2, O_2)$ can then be determined by means of numerical iteration.
2. It is possible to obtain further information by means of additional measurement of the heat conductivity at different temperatures. Possibly, the concentrations $xN_2$ and $xO_2$ can thereby be determined separately.
3. It is possible to obtain additional information by means of additional measurement of the heat capacity (optionally at different temperatures). Possibly, the concentrations $xN_2$ and $xO_2$ can thereby be determined separately.

Literature

[1] Analyse und Bewertung der Nutzungsmöglichkeiten von Biomasse {Analysis and evaluation of the utilization possibilities of biomass}, Wuppertal Institut für Klima Umwelt Energie {Wuppertal Institute for Climate, Environment, Energy}, 2005
[2] DVGW Arbeitsblatt G262 {DVGW Work Paper G262}: Nutzung von Gasen aus regenerativen Quellen in der öffentlichen Gasversorgung {Utilization of gases from regenerative sources in the public gas supply}

The invention claimed is:

1. Method for determining the gas quality of a sample gas mixed at least in part with biogas or processed biogas, having the main components $CH_4$, $CO_2$, $N_2$, $O_2$, and $H_2$, proceeding from a spectrum of the sample gas determined via at least one infrared-spectroscopy device, under operating conditions, from which the mole ratios of the sample gas are determined via a correlation calculation performed by a computer, and converted via the computer to characteristic variables of the gas quality, wherein the spectrum comprises an optical absorption of methane $CH_4$ and carbon dioxide $CO_2$ of the sample gas, and, if liquid gas LPG is mixed in, the optical absorption of the LPG, and the heat conductivity $\lambda$ is measured, wherein the mole ratio $xCH_4$ is determined via the computer from the absorption of the $CH_4$, the mole ratio $xCO_2$ is determined via the computer from the absorption of the $CO_2$, and, if liquid gas LPG is mixed in, the mole ratio xLPG is determined via the computer from the absorption of the LPG, wherein the mole ratios of nitrogen $xN_2$, of oxygen $xO_2$ and of hydrogen $xH_2$ that are not detected optically are determined from the mole ratios $xCH_4$, $xCO_2$ and the heat conductivity $\lambda$, and, if liquid gas LPG is mixed in, from the mole ratio xLPG, via the correlation calculation performed by the computer, the correlation calculation comprising $\lambda = F(xCH_4, xCO_2, xN_2, xO_2, xH_2)$ or $\lambda = F(xCH_4, xCO_2, xN_2, xO_2, xH_2, xLPG)$, and wherein characteristic parameters of the sample gas are calculated from the mole ratios obtained in this way, under the prerequisites that:

all the mole ratios together amount to 100% of the sample gas, and the mole ratios $xN_2$ of $N_2$ and $xO_2$ of $O_2$ are determined as a sum.

2. Method according to claim 1, wherein the characteristic variables comprise at least one member selected from the group consisting of: gross calorific value, net calorific value, density, Wobbe index, and methane number.

3. Method according to claim 1, wherein a linear formula for the correlation calculation $\lambda=F(xCH_4, xCO_2, xN_2, xO_2, xH_2)$ is selected from among the mole ratios:

$$\lambda=\lambda_0+xCH_4.\lambda CH_4+xCO_2.\lambda CO_2+xN_2.\lambda N_2+xO_2.\lambda O_2+xH_2.\lambda H_2.$$

4. Method according to claim 1, wherein when LPG is mixed into the sample gas, a linear formula for the correlation calculation $\lambda=F(xCH_4, xCO_2, xN_2, xO_2, xH_2, xLPG)$ is selected from among the mole ratios:

$$\lambda=xCH_4.\lambda CH_4.+xCO_2.\lambda CO_2+xN_2.\lambda N_2+xO_2.\lambda O_2+xH_2.\lambda H_2+xLPG.\lambda LPG.$$

5. Method according to claim 1, wherein a polynomial formula for the correlation calculation $\lambda=F(xCH_4, xCO_2, xN_2, xO_2, xH_2)$ or $\lambda=F(xCH_4, xCO_2, xN_2, xO_2, xH_2, xLPG)$ is selected from among the mole ratios, with terms of a higher order and mixed terms.

6. Method according to claim 5, wherein the solution of the formula of the correlation calculation takes place by way of a polynomial formula, via numerical iteration performed by the computer.

7. Method according to claim 1, wherein the measured heat conductivity $\lambda_m$ and the calculated heat conductivity $\lambda$ are compared with one another via iterative variation performed by the computer and calculation by the computer of the unknown mole ratios $xN_2$, $xO_2$, and $xH_2$.

8. Method according to claim 7, wherein the mole ratios being sought are determined by the computer when the measured heat conductivity $\lambda_m$ and the calculated heat conductivity $\lambda$ are equal.

9. Method according to claim 1, wherein the mole ratios $xN_2$ of $N_2$ and $xO_2$ of $O_2$ are determined from the correlation performed by the computer as a sum $x(N_2,O_2):=xN_2+xO_2$.

10. Method according to claim 1, wherein the heat conductivity of the sample gas is measured at two temperatures ($\lambda 1$, $\lambda 2$), the heat capacity of the sample gas is measured at two temperatures (C1, C2), and the mole ratios $xCH_4$, $xCO_2$, $xN_2+xO_2$, and $xH_2$ are determined via the computer solving a system of correlation equations:

$$\lambda 1=F1(xCH_4, xCO_2, xN_2, xO_2, xH_2),$$

$$\lambda 2=F2(xCH_4, xCO_2, xN_2, xO_2, xH_2),$$

$$C1=F3(xCH_4, xCO_2, xN_2, xO_2, xH_2), \text{ and}$$

$$C2=F4(xCH_4, xCO_2, xN_2, xO_2, xH_2).$$

11. Method according to claim 1, wherein the heat conductivity $\lambda$ is measured at multiple temperatures of the sample gas, in order to individually determine the mole ratios of $xN_2$ and $xO_2$.

12. Method according to claim 1, wherein in addition, the heat capacity of the sample gas is measured, in order to individually determine the mole ratios of $xN_2$ and $xO_2$.

13. Method according to claim 12, wherein the heat capacity is measured at multiple temperatures of the sample gas.

14. Method according to claim 1, wherein the at least one infrared-spectroscopy device comprises a spectral filter for determining the proportions of the hydrocarbons, the spectral filter working in the range of essentially 3.33 μm.

15. Method according to claim 1, wherein the gas quality is monitored with regard to the concentration of oxygen $O_2$ and hydrogen sulfide $H_2S$ via at least one concentration-measuring device.

16. Method according to claim 15, wherein the at least one concentration-measuring device comprises chemical sensors comprising electrochemical cells.

17. Method according to claim 15, wherein the at least one concentration-measuring device comprises laser diodes.

* * * * *